United States Patent [19]

Hope

[11] Patent Number: Plant 5,921

[45] Date of Patent: Mar. 31, 1987

[54] IMPATIENS PLANT NAMED VISTA SALMON AND WHITE

[75] Inventor: Claude Hope, Cartago, Costa Rica

[73] Assignee: Ball Pan Am Plant Company, Parrish, Fla.

[21] Appl. No.: 566,501

[22] Filed: Dec. 29, 1983

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of impatiens plant named Vista Salmon and White, characterized by its very large and bright salmon-rose flowers having white eyes, profuse flowering habit, early maturing, medium-green foliage, vigorous growth rate, excellent self-branching, and by its tall and spreading habit, making the cultivar suitable for bedding plants, pot plant culture and hanging baskets.

2 Drawing Figures

The present invention relates to a new and distinctive cultivar of impatiens plant, botanically known as Impatiens, and known by the cultivar name Vista Salmon and White. The new cultivar resulted from a planned program of hybridization for the purpose of obtaining a series of plants having a wide range of colors and very large flowers derived from the New Guinea complex of species collected by the Longwood Garden Expedition of 1970. The new cultivar was referred to during the selection process as seedling No. 3188-42-2, and was selected in 1981. The new cultivar was produced from a cross of seedling No. 1962-29 (from Impatiens Mooreana)×1659-2-1-3 (from Impatiens Schlecterii P.I. 354260).

Asexual reproduction by terminal or stem cuttings taken by me at Cartago, Costa Rica has shown that the unique features of this new impatiens are stabilized and are reproduced true to type in successive propagations.

The following characteristics distinguish the new impatiens from both its parent varieties and other cultivated impatiens of this type known and used in the floriculture industry:

1. Vista Salmon and White was selected and is principally characterized by its very large (74 mm.) and salmon-rose flowers, which bloom early in its development and are abundant in number.

2. Foliage is a medium-green color which provides an excellent background and contrast for the flowers.

3. Habit is somewhat tall (45–55 cm. when full grown) and spreading, making the cultivar ideal for bedding plants, pot plant culture and hanging baskets.

4. Rate of growth is fast and vigorous, producing in 6–8 weeks a saleable plant 30–35 cm. tall and 40 cm. in diameter for a 5½" pot.

5. Flowers have an attractive white eye.

6. Excellent self-branching habits.

7. Good keeping qualities exhibited when grown outdoors in full sun during spring, fall and winter, and under light shade in the summer months in Florida.

The accompanying colored photographs illustrate the overall and close up appearances of the new cultivar, showing the colors as true as it is reasonably possible to obtain in colored reproductions of this type.

Sheet 1 comprises a color photograph showing the new cultivar in perspective view. The flower color in sheet 1 is somewhat more pink and less salmon than the true flower color during cool finishing periods.

Sheet 2 comprises an enlarged black and white photograph with one flower depicting the true flower color in late August. The flower color during high light and temperature periods is somewhat lighter than during cooler finishing periods.

The following is a detailed description of my impatiens cultivar based on plants produced under commercial practice in Cortez and Parrish, Fla. The plants were grown outdoors in full sun during spring, fall and winter months and under light shade during the summer months. Color references are made to The Royal Horticultural Society Colour Chart except where general terms of ordinary dictionary significance are used.

Parentage: Seedling No. 1962-29 (from Impatiens Mooreana P.I. 366030)×1659-2-1-3 (from Impatiens Schlecterii P.I. 354260).

Propagation:

A. *Type cutting.*—Tip cuttings with stems of 5 cm.

B. *Time to initiate roots.* 10–14 days at 27° C. summer; 12–16 days at 18° C. winter.

C. *Rooting habit.*—Abundant and fibrous.

Plant Description:

A. *Form.*—Tall and spreading, broad dome-shaped.

B. *Habit of growth.*—Rate of growth is moderate to fast for this type of plant. Vegetative shoots are formed at lower nodes and flowers at the higher nodes.

C. *Foliage description.*—Lower leaves opposite, higher leaves in whorls of 5–7. Leaves are simple. (1) Size: Average full grown leaf is 125 mm. long×41 mm. wide. Full grown leaves have petioles, 17 mm. long; young leaves have 5–7 mm. long petioles. (2) Shape: Elliptic; apex acute; base attenuate. (3) Texture: Smooth surface, glabrous. (4) Margin: Serrulate. (5) Color: young foliage, top side yellow green 144A to green 143A, under side yellow-green 146C; mature foliage, top side green 137A, under side greyed green 191A. (6) Venation: Pinnate; main vein close to yellow green 149D.

Flowering description:

A. *Flowering habits.*—Very floriferous, flowers occurring progressively around the whorl of leaves. Flowers are large and single.

B. *Natural flowering season.*—Flowering is indeterminate and occurs throughout the year except for periods of high light and high temperature in Florida.

C. *Flower bud description.*—Conical, covered with 3 sepals, upper two sepals are 11 mm. long×6 mm. wide, apex acuminate. Lower sepal 14 mm. long×7 mm. wide, apex acuminate. Upper sepals are green and lower sepal colorless infused with green. Hollow spur 41 mm. long on bud, 50 mm. long when full grown, connected to lower sepal. Spur is colorless infused with pink.

D. *Flowers borne.*—On peduncles 55 mm. long, green in color.

E. *Quantity of flowers.*—One flower per leaf, occurring progressively around the whorl of leaves.

F. *Petals.*—(1) Shape: Top petal heart-shaped with a wide rounded base (no point). All other petals heart-shaped. Occasionally, petals are heart-shaped with a lobe (small) where petal curves to form the heart shape. (2) Color: In fall, winter and spring under cooler finishing temperatures, top side red 52C when opening, with a light to white eye, fading to close to and between 52C and 52D, with nearly decomposed petals being close to red 55B; under side close to 52D; in summer, top side when opening 51D, with white center. (3) Number of petals; Five. (4) Size of flowers: Top petal 25 mm. long×35 mm. wide; 2 middle petals 39 mm. long×29 mm. wide. Total flower diameter is 73 mm.

G. *Reproductive organs.*—(1) Stamens: Five in number, with the lower stamen being shorter than the other stamens. Stamens united in an asymmetrical tube surrounding and covering the ovary. (a) anther shape: hooded, colorless infused with pink. (b) pollen color: cream. (2) Pistels: (a) stigma shape; Five pointed star, colorless. (b) styles: Very short; cream color infused with pink. (c) Ovaries: 5, celled, size 5–8 mm., green in color with slight pink stripe.

Disease resistance: No general plant diseases noted. Insect problems can include the two spotted spider mite which can cause foliar injury and thrips which can cause stunting and injury of the growing tip.

I claim:

1. A new and distinct cultivar of impatiens plant named Vista Salmon and White, as described and illustrated, and particularly characterized by its very large and bright salmon-rose flowers having white eyes, profuse flowering habit, early maturing, medium-green foliage, vigorous growth rate, excellent self-branching, and by its tall and spreading habit, making the cultivar suitable for bedding plants, pot plant culture and hanging baskets.

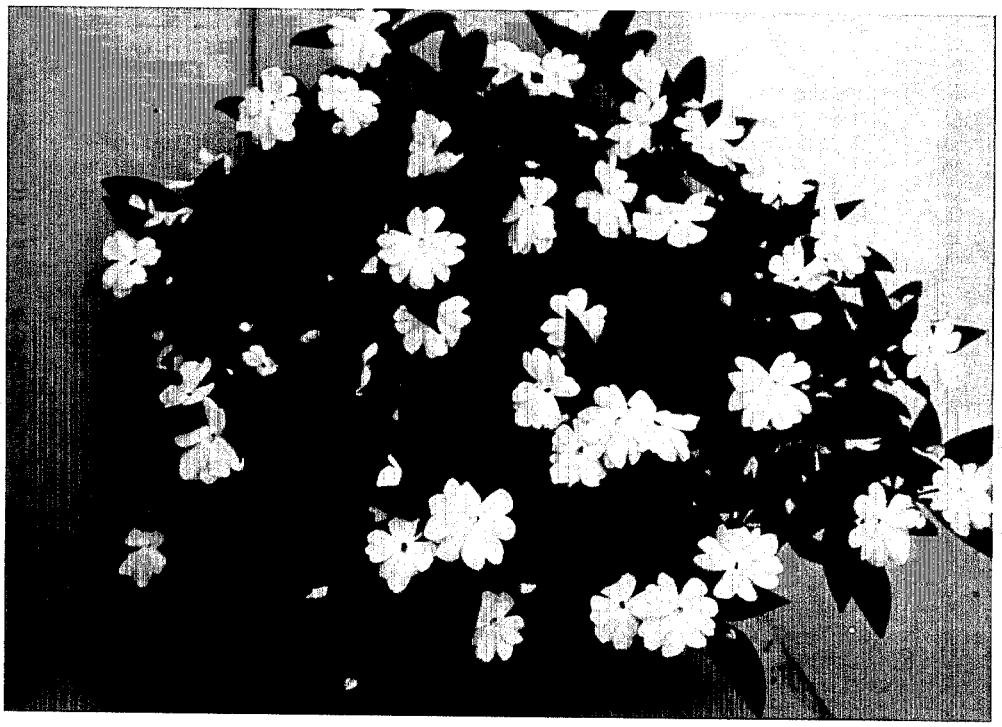

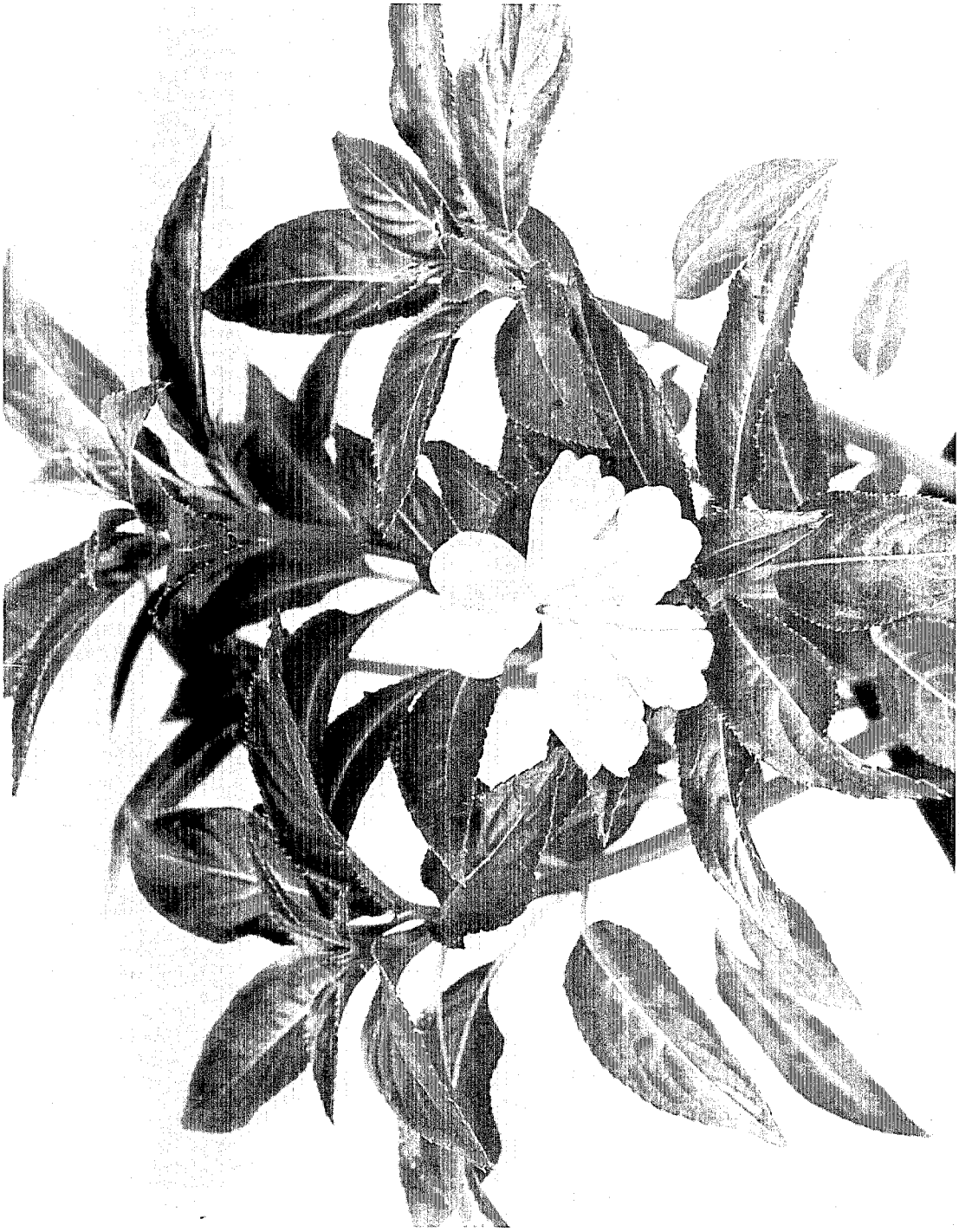

* * * * *